United States Patent
Keast et al.

(10) Patent No.: US 11,957,308 B2
(45) Date of Patent: *Apr. 16, 2024

(54) MEDICAL APPLIANCE FOR CONTROLLING MEDICAL DEVICE THROUGH CATHETER SHEATH BASED ON PNEUMATIC ACTION

(71) Applicant: Broncus Medical Inc., San Jose, CA (US)

(72) Inventors: Thomas M. Keast, Sunnyvale, CA (US); Eric Gwerder, San Jose, CA (US); Henky Wibowo, San Jose, CA (US)

(73) Assignee: BRONCUS MEDICAL INC., San Jose, CA (US)

( * ) Notice: Subject to any disclaimer, the term of this patent is extended or adjusted under 35 U.S.C. 154(b) by 116 days.

This patent is subject to a terminal disclaimer.

(21) Appl. No.: 17/166,953

(22) Filed: Feb. 3, 2021

(65) Prior Publication Data

US 2021/0153726 A1 May 27, 2021

Related U.S. Application Data

(62) Division of application No. 15/714,725, filed on Sep. 25, 2017, now Pat. No. 10,939,805.

(51) Int. Cl.
| | | |
|---|---|---|
| A61B 1/00 | (2006.01) | |
| A61B 1/005 | (2006.01) | |
| A61B 1/267 | (2006.01) | |
| A61B 10/02 | (2006.01) | |
| A61B 18/00 | (2006.01) | |
| A61B 18/14 | (2006.01) | |
| A61B 90/00 | (2016.01) | |
| A61M 25/00 | (2006.01) | |
| A61M 25/01 | (2006.01) | |

(Continued)

(52) U.S. Cl.
CPC ........ *A61B 1/00133* (2013.01); *A61B 1/0051* (2013.01); *A61B 10/0283* (2013.01); *A61B 18/1492* (2013.01); *A61B 1/2676* (2013.01); *A61B 2018/00577* (2013.01); *A61B 2018/00982* (2013.01); *A61B 2018/1475* (2013.01); *A61B 2090/0811* (2016.02); *A61M 25/0026* (2013.01); *A61M 25/01* (2013.01); *A61M 25/0113* (2013.01); *A61M 25/0155* (2013.01); *A61M 2025/0681* (2013.01); *A61M 25/09041* (2013.01)

(58) Field of Classification Search
CPC .............. A61B 1/00133; A61B 1/0051; A61B 10/0283; A61B 18/1492; A61B 2018/00577
See application file for complete search history.

(56) References Cited

U.S. PATENT DOCUMENTS

| | | |
|---|---|---|
| 4,274,408 A | 6/1981 | Nimrod |
| 5,396,880 A | 3/1995 | Kagan et al. |
| 5,487,757 A | 1/1996 | Truckai et al. |

(Continued)

*Primary Examiner* — Puya Agahi
(74) *Attorney, Agent, or Firm* — Batt IP A Law Corporation; Richard Batt

(57) ABSTRACT

A medical appliance for use in medical procedures to controllably advance a medical device through a sheath. The medical appliance features pneumatic action and connecting structures adapted to couple the appliance to a variety of types of catheters, tools, and instruments.

17 Claims, 9 Drawing Sheets

(51) Int. Cl.
*A61M 25/06* (2006.01)
*A61M 25/09* (2006.01)

(56) References Cited

U.S. PATENT DOCUMENTS

| | | |
|---|---|---|
| 5,843,091 A | 12/1998 | Holsinger et al. |
| 6,692,494 B1 | 2/2004 | Cooper et al. |
| 7,022,088 B2 | 4/2006 | Keast et al. |
| 7,431,189 B2 | 10/2008 | Shelton, IV et al. |
| 8,235,944 B2 | 8/2012 | Gharib |
| 8,409,167 B2 | 4/2013 | Roschak |
| 8,517,955 B2 | 8/2013 | Keast et al. |
| 8,676,301 B2 | 3/2014 | Coyle |
| 9,072,823 B2 | 7/2015 | Hopman et al. |
| 2008/0064920 A1 | 3/2008 | Bakos et al. |
| 2012/0289815 A1 | 11/2012 | Keast et al. |
| 2013/0310833 A1* | 11/2013 | Brown ........... A61B 17/320016 606/45 |
| 2014/0305196 A1 | 10/2014 | Ellis et al. |
| 2015/0005662 A1 | 1/2015 | Brik et al. |
| 2018/0289388 A1* | 10/2018 | Lenker ........... A61B 17/320016 |

\* cited by examiner

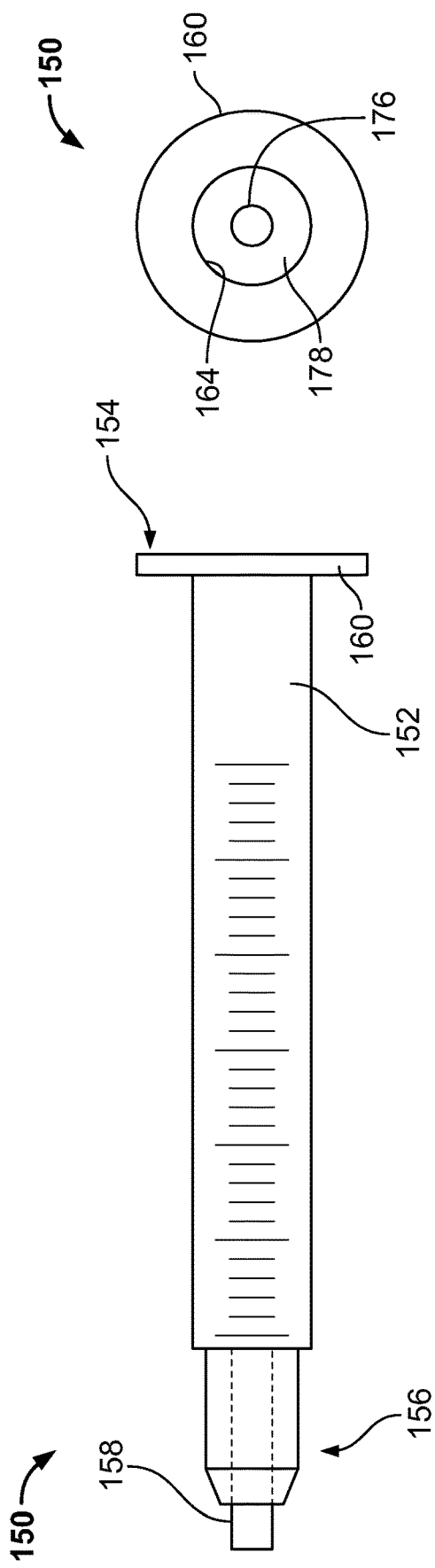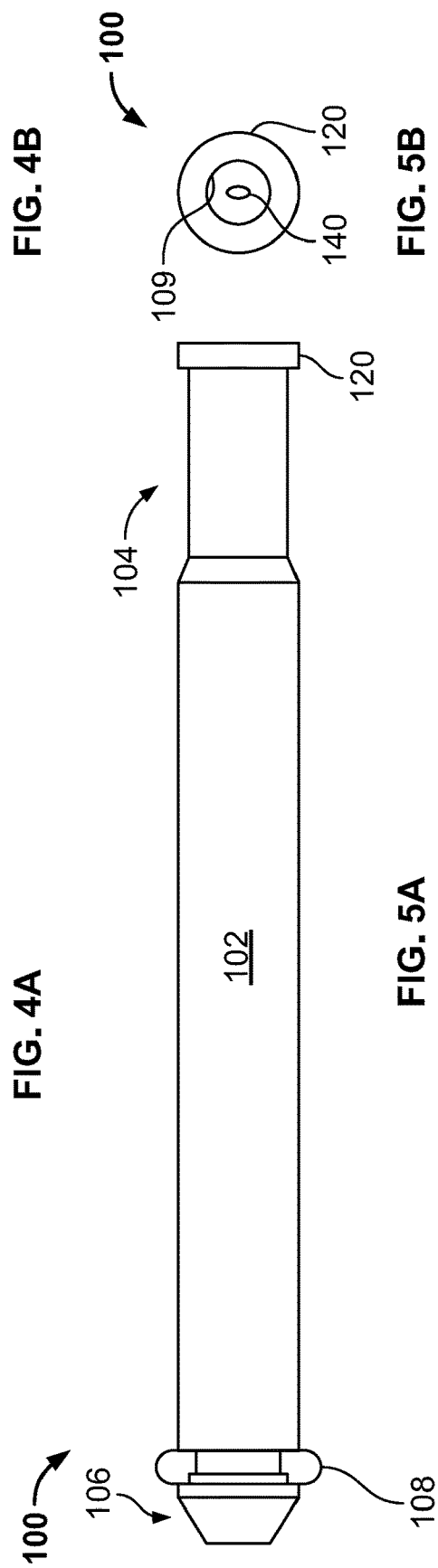

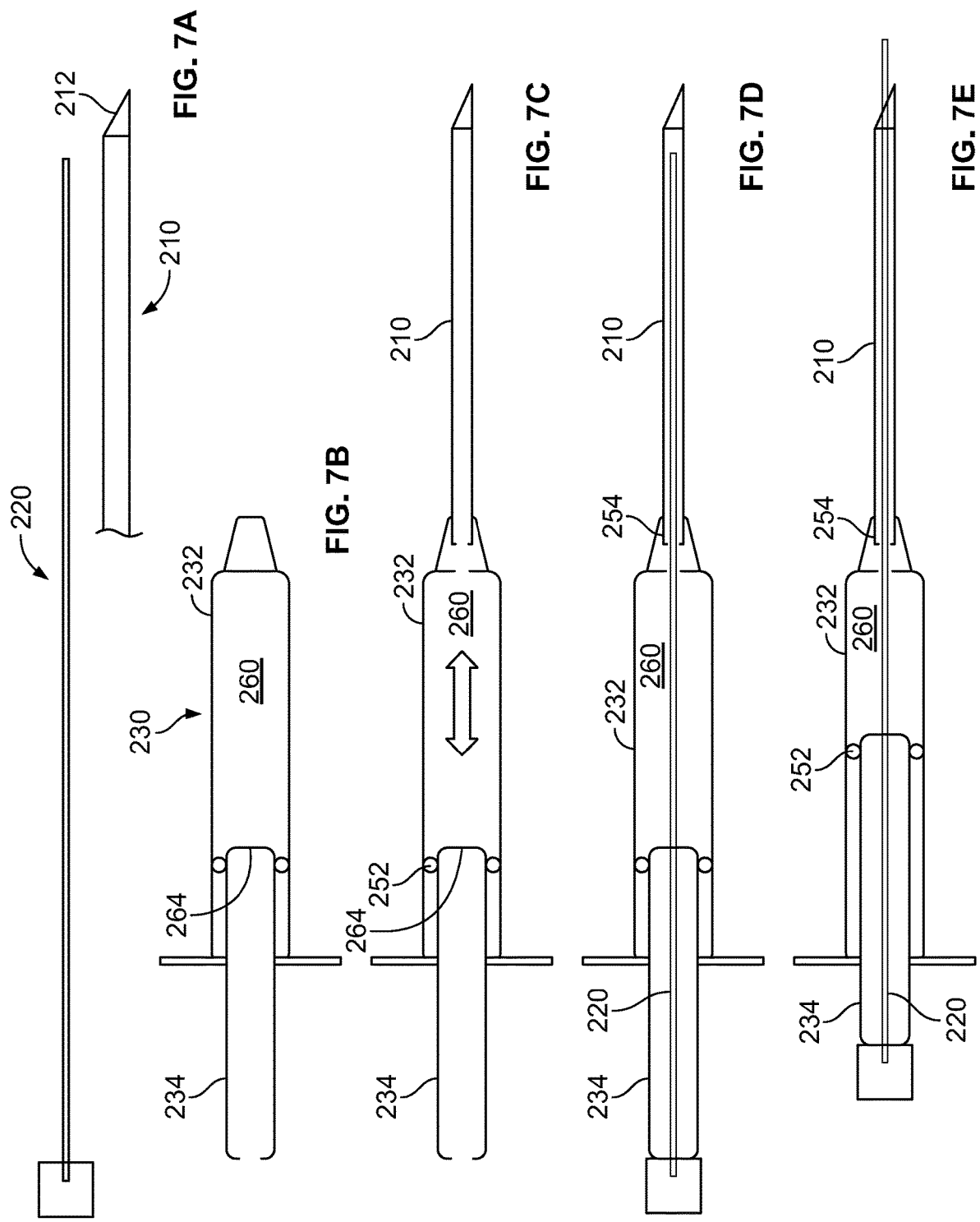

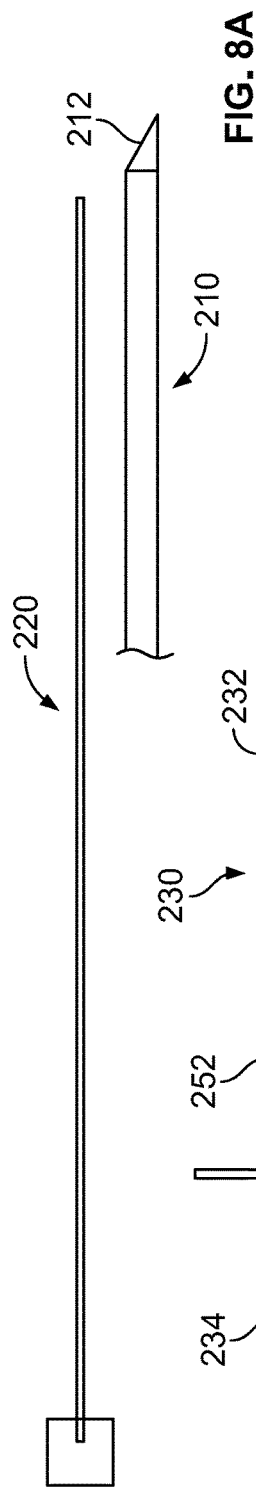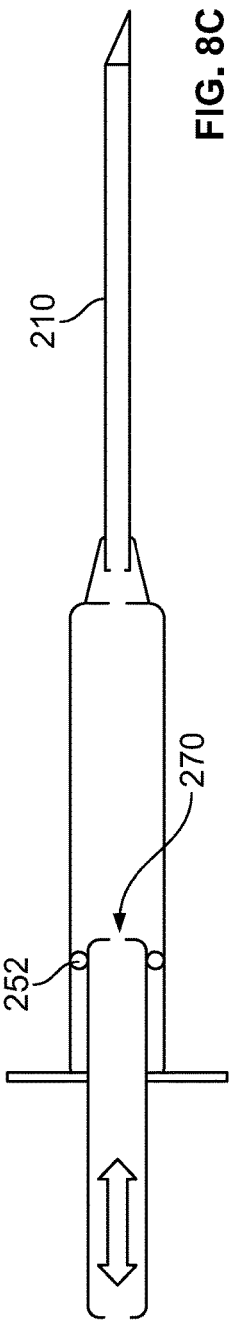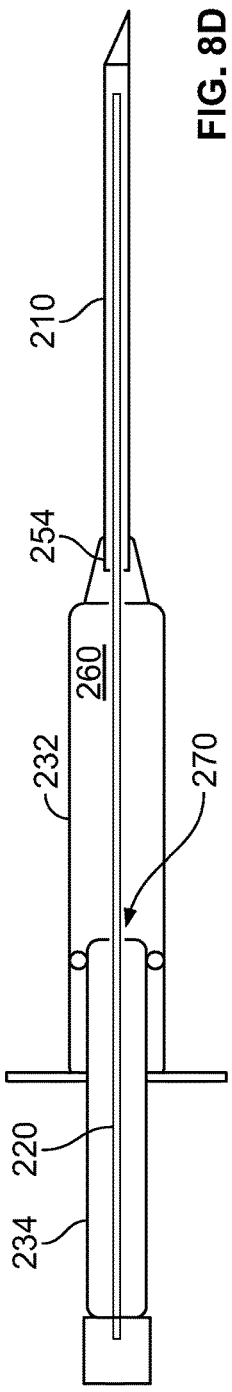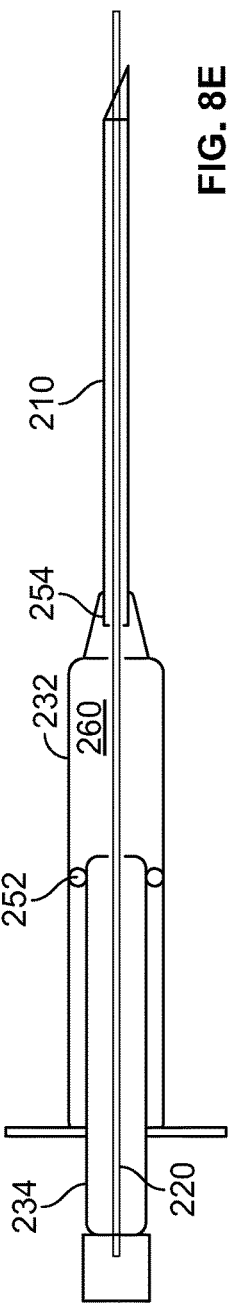

MEDICAL APPLIANCE FOR CONTROLLING MEDICAL DEVICE THROUGH CATHETER SHEATH BASED ON PNEUMATIC ACTION

CROSS-REFERENCE TO RELATED APPLICATIONS

This is a divisional patent application of non-provisional U.S. patent application Ser. No. 15/714,725, filed Sep. 25, 2017, entitled "MEDICAL APPLIANCE FOR CONTROLLING MEDICAL DEVICE THROUGH CATHETER SHEATH BASED ON PNEUMATIC ACTION."

BACKGROUND OF THE INVENTION

In endoscopic surgery, a scope is advanced through small incisions or natural body openings to diagnose and treat disease. A diagnostic or treatment tool is then advanced through the working channel of the scope to the target tissue. Frequently, the instrument or tool for performing the procedure includes an outer sheath to protect the working channel of the scope and to facilitate positioning of the procedural tool at the target location. The physician typically advances the inner tool by hand through the sheath until the working tip reaches the target. Once the position is confirmed, the working tool is activated to carry out the procedure.

Despite the acceptance by physicians of performing endoscopic procedures, a number of challenges remain not the least of which is the ability to precisely move the inner tool relative to the outer sheath. The inner tool is difficult to move a precise measured distance. Additionally, the types of inner tools vary widely and depend on the procedure desired. A physician needs a custom accessory for each type of sheath and/or inner tool. This is undesirable.

Various approaches attempt to address some of the above mentioned challenges. For example, approaches to move an inner tool relative to the outer sheath are described in U.S. Pat. Nos. 9,072,823; RE34,086; 8,676,301; 8,235,944; 5,843,091; 5,396,880; 4,274,408 and US patent publication no. 20150005662.

Notwithstanding the above, there is still a need for improved surgical devices, methods, and systems for controllably advancing a procedural tool through an outer flexible catheter sheath.

SUMMARY OF THE INVENTION

A system and method for assisting a physician to controllably advance a medical device through a catheter sheath.

In embodiments, a medical appliance couples the catheter sheath to the medical device and has pneumatic force generating means to impart motion to the medical device. In embodiments, the pneumatic action arising from the appliance causes a first motion selected from the group including rotation, advancement, retraction, flexure, and bend. In embodiments, the pneumatic action arising from the appliance causes advancement of the medical device a precise measured distance from the catheter sheath.

In embodiments, an appliance includes an outer body having a proximal end, a distal end, a cavity extending through the body from the proximal end to the distal end, and a first connecting structure to detachably join the outer sheath to the outer body. The appliance further includes an inner member movably disposed within the cavity of the outer body, and a second connecting structure on the inner member to detachably join to the inner tool. At least one actuator extends from the appliance for a physician to manipulate the outer body relative to the inner member.

In embodiments, the appliance further comprises a first elastic sealing portion disposed in an interface between the cavity of the outer body and the inner member.

In embodiments, the appliance further comprises a second sealing portion located in the inner member to contact the inner tool when the inner tool is advanced into and through the lumen of the inner member.

In embodiments, the appliance is adapted to be compatible with a wide range of devices and in some embodiments, the appliance is configured to be coupled to Luer lock type adapters.

In embodiments, the appliance includes hermetical sealing portions and provides for aspiration and expression of a tissue sample from the end of the tool.

In embodiments, a medical catheter system for performing a medical procedure comprises an outer sheath, a working tool, and a pneumatic appliance detachably coupled to the outer sheath and detachably coupled to the medical device. Movement of the plunger in the appliance controllably and precisely moves the inner tool relative to the sheath.

In embodiments, a method for assisting a physician to controllably advance a medical tool through an outer flexible catheter sheath comprises the steps of: providing an appliance comprising a barrel shaped outer body and an inner plunger member slideably moveable within the outer body; connecting the appliance to both the outer flexible catheter and the medical tool; and actuating the appliance to controllably move the medical tool relative to the sheath.

In embodiments, a method for assisting a physician to controllably guide a medical device through a catheter sheath comprises the steps of coupling the medical device to a pneumatic force generator; inserting the medical device into the catheter sheath; and controlling a pneumatic force in the pneumatic force generator to increase the pneumatic force to create a first motion or to decrease the pneumatic force to create a second motion.

In embodiments, the first motion causes a corresponding movement of the medical device. The first motion can include advancement, retraction, or rotation.

The order of the steps may vary except where logically impermissible. In embodiments, for example, the coupling step precedes the inserting step.

In embodiments, the step of controlling the appliance to guide or move the medical device excludes robotic motion.

The description, objects and advantages of the present invention will become apparent from the detailed description to follow, together with the accompanying drawings.

BRIEF DESCRIPTION OF THE DRAWINGS

FIG. 4A is a front view of a first component of an appliance in accordance with an embodiment of the invention.

FIG. 4B is a right-side view of the first component of an appliance shown in FIG. 4A.

FIG. 5A is a front view of a second component of an appliance in accordance with an embodiment of the invention.

FIG. 5B is a right-side view of the second component of an appliance shown in FIG. 5A.

FIGS. 7A-7E are illustrations of components of a medical device system to control motion of a stylet through a needle catheter by pneumatic action.

FIGS. 8A-8E are illustrations of components of a medical device system to control motion of a stylet through a needle catheter similar to the system shown in FIGS. 7A-7E except the pneumatic appliance includes an unsealed lumen for accommodating the stylet.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

Figure 1:
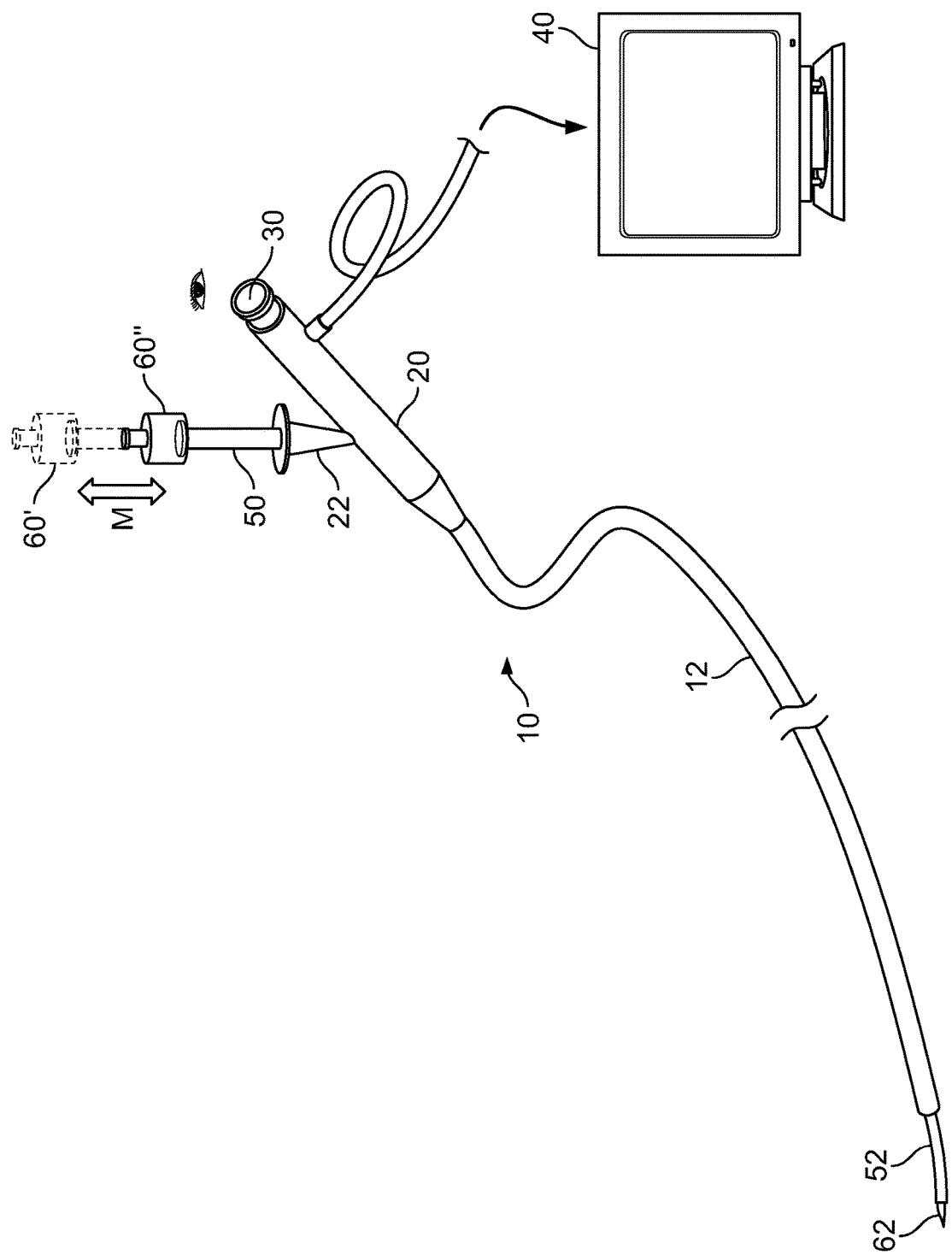
FIG. 1 is an illustration of a bronchoscope system, catheter sheath, and an inner tool member extending therefrom.
Figure 2A:
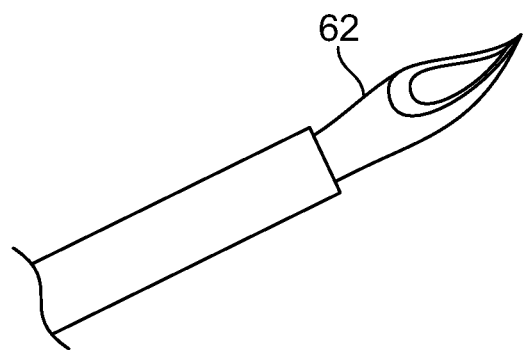
FIGS. 2A-2I are illustrations of various inner tools which may be used in combination with the catheter sheath.
Figure 2B:
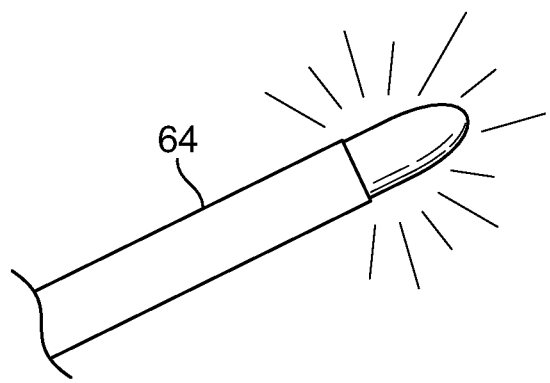
Figure 2C:
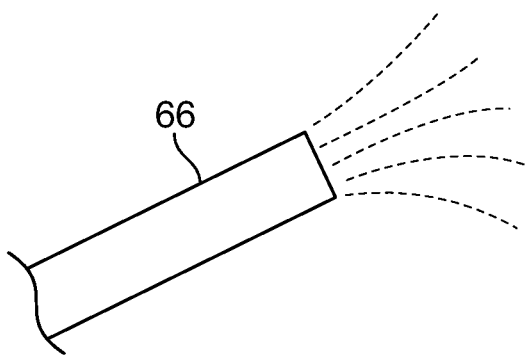
Figure 2D:
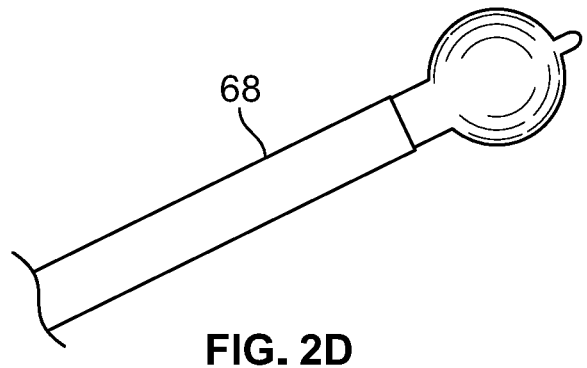
Figure 2E:
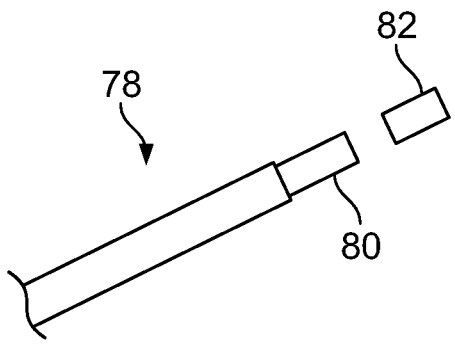
Figure 2F:
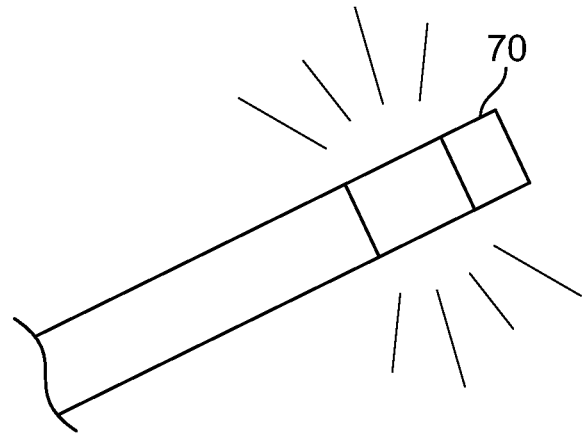
Figure 2G:
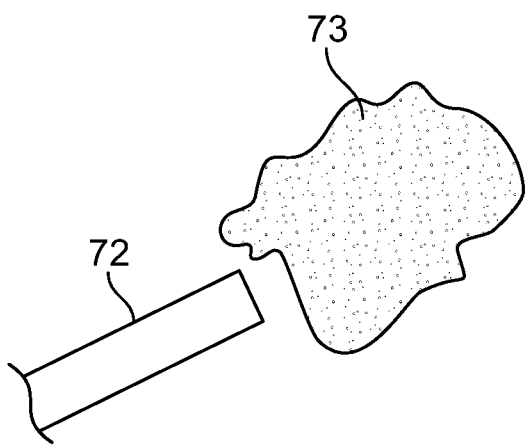
Figure 2H:
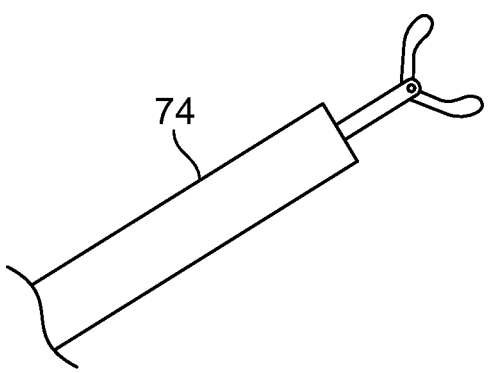
Figure 2I:
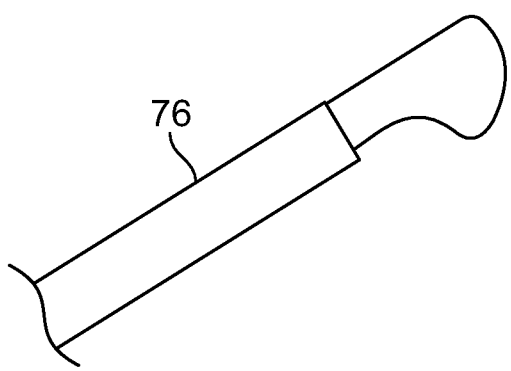

With reference to FIG. 1, a bronchoscope system 10 is illustrated. Bronchoscope system 10 is shown having a flexible shaft 12, a scope handle 20, hub 22 for accepting ancillary tools, eyepiece 30, and a video monitor for showing live images of the anatomy observed by a camera incorporated into the distal end of the shaft.

A catheter sheath 50 is shown advanced through the hub 22 of the scope. A distal portion of the sheath 52 is shown extending from the bronchoscope shaft 12.

An inner medical device/tool 60 is advanced through outer sheath 50. Inner tool tip 62 is shown protruding from the distal section of the outer sheath 52. In an exemplary procedure, the physician manually manipulates (M) handle hub 60' of the inner tool from a retracted position to a forward/distal position 60" and vice versa. The hub 60' may include a mating feature (e.g., a Luer compatible structure) to accept and lock to the rim of the outer sheath 50.

The inner tool is shown as a needle 62 such as a biopsy needle. However, it is to be understood that the tool may vary widely and be in the form of another medical device. With reference to FIGS. 2A-2I, examples of tools include, without limitation: needles whether for biopsy or otherwise 62, ablation catheter 64 whether electrosurgical, microwave, or cryogenic-based, drug or therapeutic agent delivery catheter 66, dilation instruments 68, optical or vision probes 70 whether based on ultrasound or other imaging means, vapor delivery catheter 72 for delivering a condensable vapor 73, forceps 74, brushes, snare 76, stylet, guidewire, temperature probes, ultrasound probes, implant delivery catheter 78 and pusher 80 whether for fiducial 82 or radioactive seed or other. Examples of catheters, implants and tools are shown and described in U.S. Pat. Nos. 6,692,494; 7,022,088; 8,409, 167 and 8,517,955; and Patent Publication No. 2012/0289815.

Figure 3:
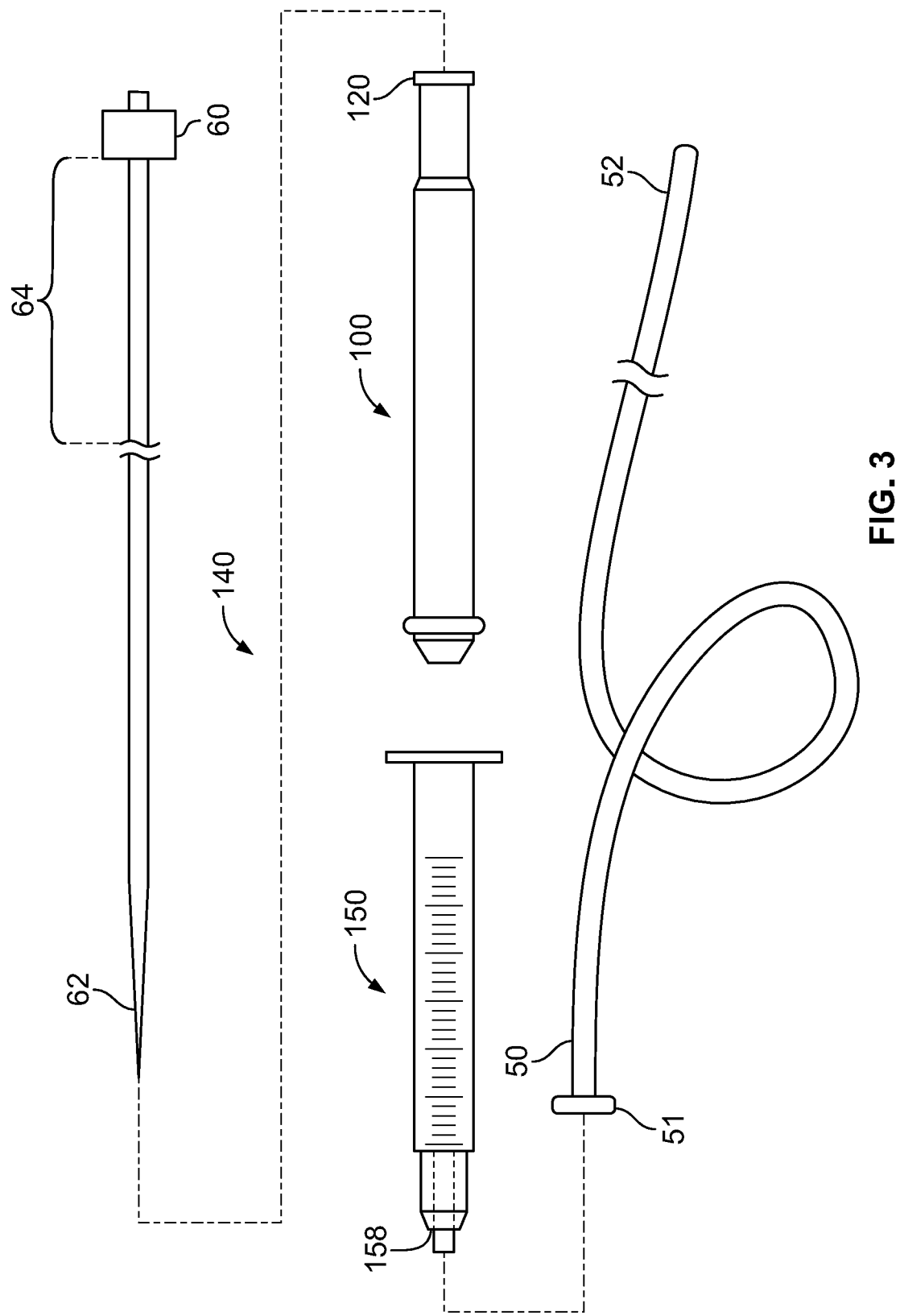
FIG. 3 is an exploded view of a catheter sheath, inner tool, and an appliance in accordance with one embodiment of the invention.

FIG. 3 is an exploded view of the outer sheath 50, rim 51, inner tool 60, and an appliance 140 in accordance with an embodiment of the invention. As discussed herein, the appliance 140 is adapted to generate pneumatic forces serving to cause motion to the inner medical device 60. The appliance shown in FIG. 3 includes a plunger component 100 that is controllably advanceable in barrel component 150. Plunger component 100 is shown having a flange 120 at proximal end for coupling to the hub 60 of the inner tool.

Barrel member 150 is shown having a distal connector 158 which is adapted to couple to the proximal rim 51 of the outer sheath 50. As further described herein, the sheath is removably coupled to the distal end of the appliance, and the inner tool is advanced into and through the appliance until the hub 60 of the tool is removably locked to the flange 120 of the plunger. The plunger may be advanced into the barrel a controllable distance thereby moving the inner tool in sync with the plunger relative to the barrel and outer sheath. In this manner, and as will be described in more detail herein, the distal tip 62 of the inner tool may be advanced a controllable distance from the distal end 52 of the outer sheath.

FIG. 4A is a front view of a first component 150 of an appliance in accordance with an embodiment of the invention. FIG. 4B is a right-side view of the first component of the appliance shown in FIG. 4A. The first component 150 is shown having a barrel or cylindrically-shaped body 152, a proximal end 154, a distal end 156, and a first connecting structure 158 on the distal end to detachably join to the proximal end of the outer sheath (not shown). The first component 150 is also shown having a cavity 164 extending through the body 152 from the proximal end to the distal end, terminating in an aperture 176. As further described herein, the outer sheath is connectable to the distal end of the barrel. Connecting structures include without limitation threads, press fits structures, Luer Lock, Tuohy borsts, barbs or resilient tabs, etc.

Radially extending from the body is an actuator 160 for a physician to grip and manipulate the barrel 150 relative to the plunger 100. The actuator shown in FIGS. 4A, 4B is shaped as a circular flange but the invention is not so limited. The actuator may take a wide variety of shapes including without limitation a hub, ring, and loop. The body of the barrel is also shown with graduations or markings to show progress or advancement of the plunger, described further herein.

FIG. 5A is a front view of a second component of an appliance in accordance with an embodiment of the invention. FIG. 5B is a right-side view of the second component of an appliance shown in FIG. 5A. The second component 100 moveably fits within the cavity 164 of the first component 150, described above. The inner second component is shown having an elongate body 102, a first end 104, a second end 106, a lumen 109 extending from the first end 104 to the second end 106, and a connecting structure 120 to detachably join to the proximal end of the inner tool (not shown) with the first end of the plunger. The connecting structures for the plunger on the distal end may be similar or different to the connecting structures described above in connection with the barrel.

The diameter of the lumen of the inner member or plunger may vary. In embodiments, the diameter of the lumen ranges from about 1 to 3 mm., and in embodiments is about 2½ mm.

The plunger 100 is shown having a first sealing portion 108 which serves to provide sealing, resistance, friction, and control movement as the plunger and barrel are moved relative to one another. The first sealing portion prohibits unintended excessive advancement or retraction of the inner tool. The first sealing portion 108 is shown as an O-ring having a slightly larger radius than the body 102 of the plunger. However, the first sealing portion may take other forms or shapes. For example, the first sealing portion 108 can be an elastic cap, washer, or like structure.

The plunger 100 is also shown having a second sealing portion 140 to contact the inner tool (not shown) when the inner tool is advanced into the lumen 109 of the plunger, and to facilitate holding the inner tool. The second sealing portion 140 is shown as an elastic slit and part of the rubber cap 106. However, the second sealing portion may have other shapes and forms including without limitation a duck bill, slit, annular, O-ring, or a combination of multiple seals.

In embodiments, at least one of the first sealing portion and the second sealing portion forms hermetic seals between the plunger and barrel and the plunger and inner tool, thus creating an internal fluid sealed chamber. The fluid sealed chamber may have an annular or another type of shape. A fluid-sealed chamber aids in sample retention or expulsion.

Figure 6A:
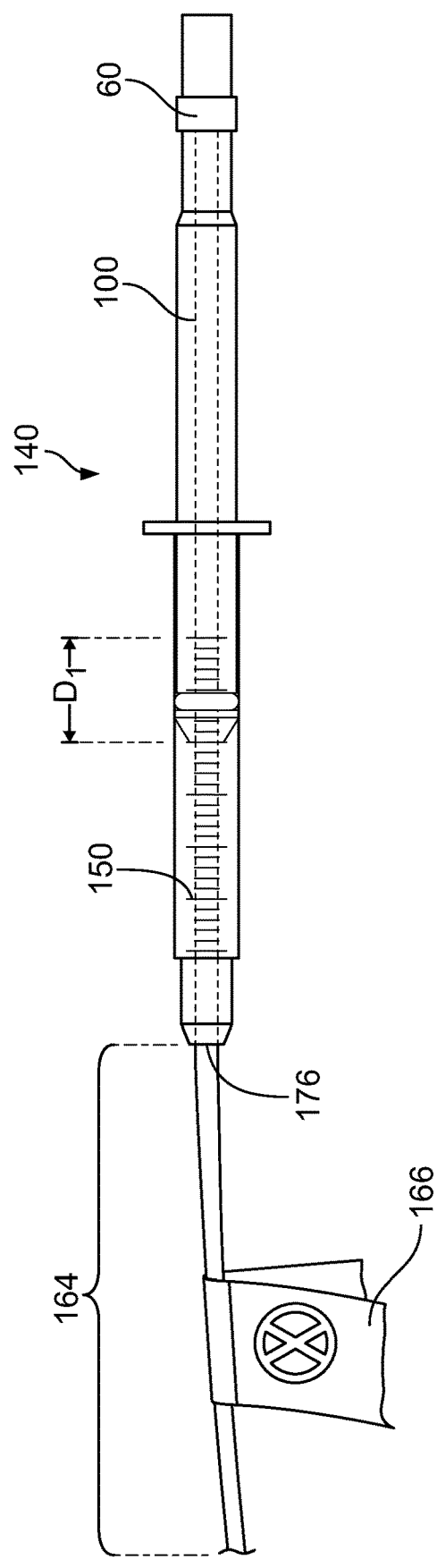
FIG. 6A is a partial front view of an appliance coupled to a procedural tool in a first or retracted position.

FIG. 6A is a partial front view of an appliance 140 coupled to a procedural inner tool 60 in a first or retracted position, with the outer sheath removed for clarity in the illustration. Inner tool 60 is detachably coupled to the proximal end of the plunger 100. In this embodiment, the connecting structures are mating Luer Lock adapters.

The shaft 164 of the inner tool is shown passing through the plunger 100, and out the distal aperture 176 of the barrel 150. A location along the shaft 164 is labeled 166 for comparing motion of the inner tool between FIGS. 6A and 6B.

Figure 6B:
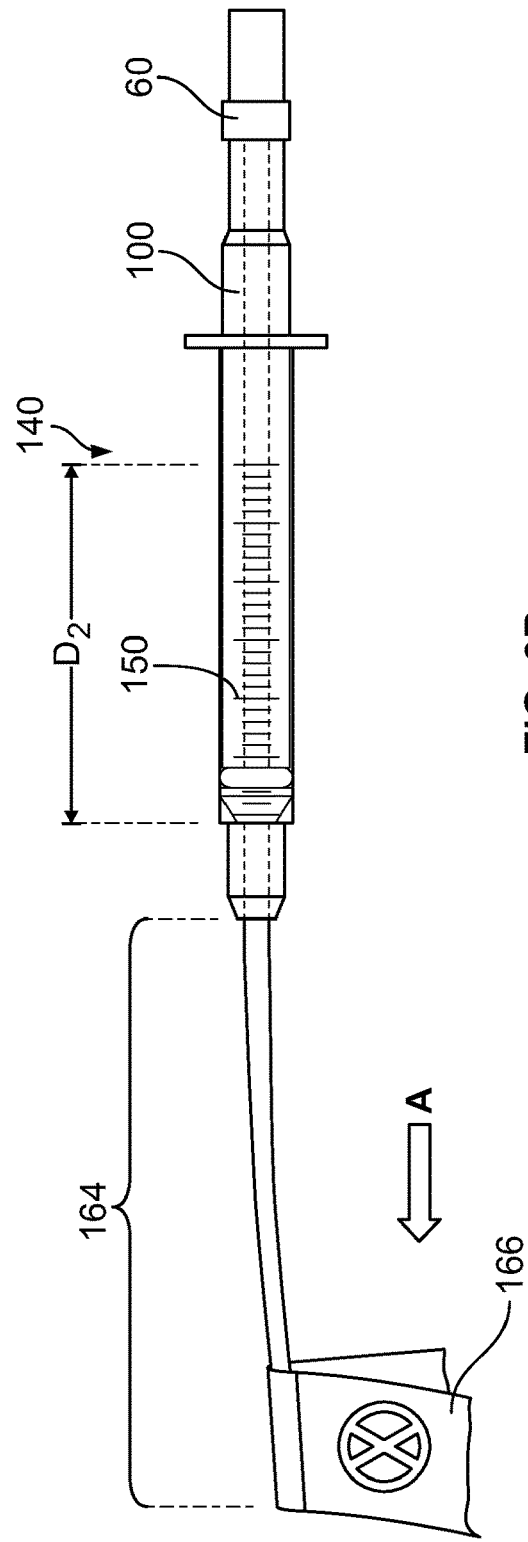
FIG. 6B is the appliance shown in FIG. 6A shown in a second or extended position.

FIG. 6B shows the appliance, and inner tool of FIG. 6A in a second or extended position. Label 166 is shown relocated in the direction (A) further from the tip of the barrel 150. The plunger 100 is shown having moved from first location D1 to second location D2. Graduation marks along the barrel illustrate movement of a particular linear distance. In an application, the physician may controllably advance the plunger relative to the barrel, thereby advancing the inner tool a precise measured distance.

In embodiments, and with reference to FIGS. 7A-7E, another appliance or adapter 230 is shown. As described herein, the adapter 230 is operable to generate pneumatic force. An outer sheath 210 comprises a needle tip 212 (e.g., the outer sheath is a needle catheter) and the inner medical device 220 is a stylet. The needle catheter 210 is attached to a barrel 232 of the adapter 230.

With reference to FIGS. 7B-7C, the plunger 234 is shown having a first sealing portion 252, and a closed sealing portion 264. Thus, when a tissue is penetrated with the needle 212, an internal fluid sealed chamber 260 is created which may be used to aspirate and express a tissue sample.

FIG. 7D shows stylet 220 attached to the plunger 234 of the adapter. The stylet 220 can be retracted or advanced by sliding the plunger 234 relative to the barrel 232. The tissue sample can be expressed in a collection vessel by advancing the stylet 220 as shown in FIG. 7E.

In embodiments, and with reference to FIGS. 8A-8E, it is possible to eliminate the hermetic seal between the inner tool 220 and plunger 234, namely, to maintain a pass-through aperture 270. This embodiment facilitates direct aspiration and expression of a tissue sample using an external device such as, for example, a syringe (not shown), attached to the plunger assembly.

Alternative Embodiments

In embodiments, the first sealing portion is hermetically sealing with the barrel. In embodiments, the first sealing portion is an O-ring forming an interference fit with the cavity of the barrel such that neither gas nor liquid is permitted to pass therethrough.

In embodiments, the second sealing portion is hermetically sealing with the shaft of the inner tool. In embodiments, the second sealing portion is a slit or duck valve which circumferentially surrounds the proximal section of the shaft of the inner tool such that neither gas nor liquid is permitted to pass therethrough.

In embodiments, the first and second components of the appliance comprise positional locking features such as, for example, indents/detents, tabs and recesses, or "J-Lock" type locking features to controllably move the components relative to one another. In embodiments, the distance is predetermined, secured, and/or fixed with a positional lock.

Figure 9A:
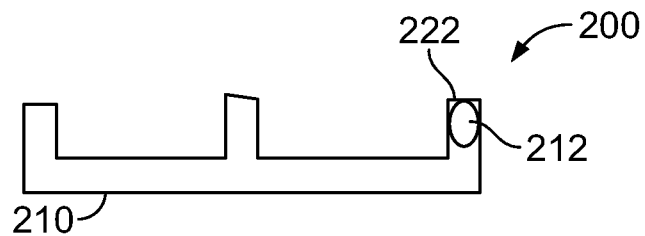
FIGS. 9A-9C are partial views of locking features of the appliance corresponding to a fully retracted, middle and fully extended positions respectively.
Figure 9B:
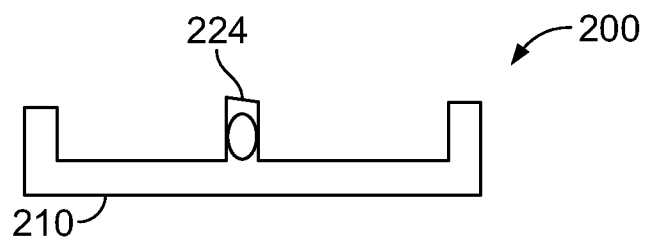
Figure 9C:
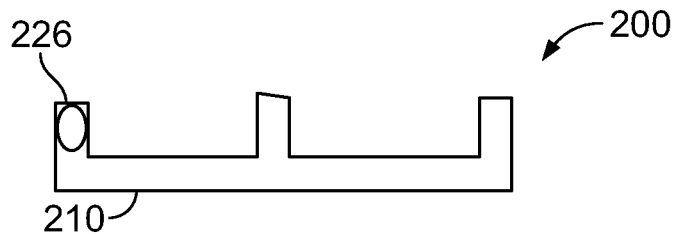

An example of a positional locking feature 200 is shown with reference to FIGS. 9A-9C. Track or guide 210 is incorporated into one of the barrel and the plunger and preferably the plunger. Track is shown in the form of a groove or slot and includes a plurality of legs 222, 224, and 226 spaced apart at predefined distances. Pin 212 on the opposing component resides movably within the track 210. The physician may move the barrel and plunger relative to one another until the pin is registered with the desired leg 222, 224, and 226 corresponding to a fully retracted, middle, and fully extended position respectively. However, it is to be understood that the locking features may vary widely, and the J-lock may also vary in features and shapes. The invention is intended to be limited only as recited in the claims appended hereto.

Another example of positional locking feature is described in U.S. Pat. No. 8,517,955 to Keast et al.

Advantages and Applications

It is to be understood that embodiments of the invention described herein provide a number of advantages including manual "by-hand" actuation in combination with controlled movement of the inner tool relative to outer sheath.

In embodiments, the medical appliance operates by pneumatic action to controllably direct the medical device or tool through a sheath. In embodiments, the invention is non-robotic.

Additionally, in embodiments, the first and second components of the appliance may cooperate with one another using various guides, channel and slide, gears (such as, for example, a rack and pinion gear, etc.) to controllably move the inner member relative to the outer body.

Additionally, in embodiments, the appliance is configured to removably couple to a wide variety of medical devices and inner tools.

In embodiments, seals (including hermetic and non-hermetic seals) are formed between the components and ancillary devices, creating an internal fluid-sealed chamber within the barrel and inner member.

Other modifications and variations can be made to the disclosed embodiments without departing from the subject invention.

We claim:

1. A medical catheter system for performing a medical procedure requiring movement between a sheath, and a medical device controllably directable through the sheath, the system comprising:
    the sheath;
    the medical device, wherein the medical device comprises a proximal end, an elongate body, and a distal surgical section; and
    a pneumatical appliance comprising a first end and a distal second end,
    wherein the distal second end of the pneumatical appliance is removably locked to a proximal end of the sheath;
    wherein the pneumatical appliance is operable to cooperate with the medical device such that the medical device extends from the first end of the pneumatical appliance, out the second end of the pneumatical appliance, and into the sheath; and
    wherein the first end of the pneumatical appliance is removably locked to the proximal end of the medical device and operable to create a force urging the medical device in a first direction relative to the sheath; and
    wherein the pneumatical appliance is operable to controllably advance the distal surgical section of the medical device from a distal end of the sheath.

2. The medical catheter system of claim 1, wherein the medical device is a stylet.

3. The medical catheter system of claim 2 wherein the sheath is a cutting sheath.

4. The medical catheter system of claim 3, wherein the cutting sheath is electrosurgical.

5. The medical catheter system of claim 1, wherein the medical device is an electrosurgical instrument.

6. The medical catheter system of claim 1, wherein the sheath is a needle, and the medical device is a stylet.

7. The medical catheter system of claim 1, further comprising an endoscope and a working channel extending through the endoscope, and the sheath and medical device being disposed through the working channel of the endoscope.

8. The medical catheter system of claim 1, wherein the pneumatical appliance comprises:
    an outer body comprising a proximal end, the distal end, a cavity extending through the outer body from the proximal end to the distal end, and a first connecting structure to detachably join to the sheath; and
    an inner member movably disposed within the cavity of the outer body, the inner member comprising an elongate body, a first end, a second end, and a lumen extending from the first end to the second end, and a second connecting structure on the inner member to detachably join to the medical device with the inner member.

9. The medical catheter system of claim 8, wherein the pneumatical appliance further comprises:
    a first elastic sealing portion disposed in an interface between the cavity of the outer body and the inner member; and
    a second sealing portion located in the inner member to contact the medical device when the medical device is advanced into and through the lumen of the inner member.

10. The medical catheter system of claim 8, further comprising graduations or marks to indicate movement of the inner member relative to the outer body.

11. The medical catheter system of claim 8, further comprising a positional locking feature for locking the inner member relative to the outer body.

12. The medical catheter system of claim 8, wherein in the outer body is barrel-shaped.

13. The medical catheter system of claim 12, wherein the inner member is plunger-shaped.

14. The medical catheter system of claim 8, further comprising a linear guide to prevent rotational motion between the inner member and outer body.

15. The medical catheter system of claim 9, wherein the first connecting structure is located at the distal end of the outer body.

16. The medical catheter system of claim 9, further comprising a hermetically sealed internal chamber formed between the first sealing portion and the second sealing portion.

17. The medical catheter system of claim 1, wherein the first direction is non-linear.

* * * * *